United States Patent
Harada et al.

(10) Patent No.: US 10,433,709 B2
(45) Date of Patent: Oct. 8, 2019

(54) IMAGE DISPLAY DEVICE, IMAGE DISPLAY METHOD, AND PROGRAM

(71) Applicant: FUJIFILM Corporation, Tokyo (JP)

(72) Inventors: Kenichi Harada, Kanagawa (JP); Yuichi Teramura, Kanagawa (JP); Kunimasa Shimizu, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 42 days.

(21) Appl. No.: 15/718,644

(22) Filed: Sep. 28, 2017

(65) Prior Publication Data

US 2018/0084970 A1   Mar. 29, 2018

(30) Foreign Application Priority Data

Sep. 28, 2016 (JP) ................................. 2016-189396

(51) Int. Cl.
*A61B 1/00* (2006.01)
*G06T 7/33* (2017.01)
(Continued)

(52) U.S. Cl.
CPC .......... *A61B 1/0005* (2013.01); *A61B 1/0002* (2013.01); *A61B 1/00006* (2013.01);
(Continued)

(58) Field of Classification Search
None
See application file for complete search history.

(56) References Cited

U.S. PATENT DOCUMENTS

| 2012/0078045 A1 | 3/2012 | Sasaki et al. |
| 2015/0009311 A1 | 1/2015 | Sasaki et al. |

(Continued)

FOREIGN PATENT DOCUMENTS

| JP | 2007-236700 A | 9/2007 |
| JP | 2012-070936 A | 4/2012 |

(Continued)

OTHER PUBLICATIONS

Extended European Search Report for corresponding Application No. 17193404.5, dated Feb. 8, 2018.
(Continued)

*Primary Examiner* — Nurun N Flora
(74) *Attorney, Agent, or Firm* — Birch, Stewart, Kolasch & Birch, LLP

(57) ABSTRACT

An image display device includes: a storage unit that stores imaging information including an endoscopic image of an imaging target organ; a connection relationship setting unit that sets a connection relationship between a plurality of endoscopic images stored in the storage unit based on the imaging information; a landmark image detection unit that detects a landmark image including a predetermined anatomical landmark as defined herein; a mapping unit that assigns the landmark image detected by the landmark image detection unit to a landmark portion of a virtual model corresponding to the imaging target organ and that assigns the plurality of endoscopic images stored in the storage unit to corresponding portions of the virtual model using the connection relationship set by the connection relationship setting unit with the landmark image as a base point; a map image generation unit as defined herein; and a display control unit as defined herein.

19 Claims, 15 Drawing Sheets

(51) Int. Cl.
   *G06T 11/60* (2006.01)
   *G06T 3/40* (2006.01)
(52) U.S. Cl.
   CPC ........ *A61B 1/00009* (2013.01); *G06T 3/4038* (2013.01); *G06T 7/337* (2017.01); *G06T 11/60* (2013.01); *A61B 1/00055* (2013.01); *G06T 2200/32* (2013.01); *G06T 2207/10068* (2013.01); *G06T 2207/20221* (2013.01); *G06T 2207/30092* (2013.01)

(56) References Cited

U.S. PATENT DOCUMENTS

| | | | |
|---|---|---|---|
| 2015/0216391 A1 | 8/2015 | Fujita et al. | |
| 2015/0313445 A1* | 11/2015 | Davidson | G06T 3/4038 600/109 |
| 2016/0000307 A1 | 1/2016 | Akimoto et al. | |
| 2016/0073927 A1 | 3/2016 | Akimoto et al. | |
| 2016/0278612 A1 | 9/2016 | Minamizato et al. | |
| 2017/0251159 A1 | 8/2017 | Ho Duc et al. | |

FOREIGN PATENT DOCUMENTS

| | | |
|---|---|---|
| JP | 2014-079376 A | 5/2014 |
| JP | 2017-534322 A | 11/2017 |
| WO | WO 2008/004222 A2 | 1/2008 |
| WO | WO 2014/168128 A1 | 10/2014 |
| WO | WO 2015/046152 A1 | 4/2015 |
| WO | WO 2015/049962 A1 | 4/2015 |
| WO | WO 2016/044624 A1 | 3/2016 |

OTHER PUBLICATIONS

Office Action dated Jun. 25, 2019 in corresponding Japanese Patent Application No. 2016-189396, with English translation.

* cited by examiner

IMAGE DISPLAY DEVICE, IMAGE DISPLAY METHOD, AND PROGRAM

CROSS-REFERENCE TO RELATED APPLICATIONS

This application claims the benefit of Japanese Patent Application JP 2016-189396, filed Sep. 28, 2016, the entire content of which is hereby incorporated by reference, the same as if set forth at length.

BACKGROUND OF THE INVENTION

1. Field of the Invention

The present invention relates to an image display device, an image display method, and a computer readable medium storing a program using an endoscopic image.

2. Description of the Related Art

In a capsule endoscope system disclosed in JP2007-236700A, a plurality of endoscopic images captured by a capsule endoscope are connected to each other based on the blood vessel patterns and superficial tissue patterns of organs appearing in the images and the imaging position of each endoscopic image. A mosaic image generated by connecting a plurality of endoscopic images to each other is displayed on a monitor in a state in which the mosaic image overlaps an anatomical outline view of each organ, in order to facilitate understanding of the correspondence relationship with each organ.

SUMMARY OF THE INVENTION

JP2007-236700A does not disclose a method of making a mosaic image and an outline view of each organ overlap each other. For example, registration between a mosaic image and an outline view of each organ can be roughly performed based on the imaging position of an endoscopic image forming the mosaic image and the outline shape of the mosaic image. In this case, however, the position of each portion of the mosaic image on the outline view of each organ is merely for convenience. Therefore, for example, in a case where an essential imaging part is set for each organ according to the examination type, even if a region on the outline view of each organ corresponding to the essential imaging part is filled with a mosaic image, it is not possible to know whether or not the essential imaging part has been actually imaged. For this reason, it is not possible to accurately evaluate omission in imaging.

The present invention has been made in view of the above circumstances, and it is an object of the invention to provide an image display device, an image display method, and a computer readable medium storing a program capable of accurately evaluating omission in imaging.

An image display device according to an aspect of the invention comprises: a storage unit that stores imaging information including an endoscopic image of an imaging target organ; a connection relationship setting unit that sets a connection relationship between a plurality of endoscopic images stored in the storage unit based on the imaging information; a landmark image detection unit that detects a landmark image including a predetermined anatomical landmark corresponding to the imaging target organ among the plurality of endoscopic images stored in the storage unit; a mapping unit that assigns the landmark image detected by the landmark image detection unit to a landmark portion of a virtual model corresponding to the imaging target organ and that assigns the plurality of endoscopic images stored in the storage unit to corresponding portions of the virtual model using the connection relationship set by the connection relationship setting unit with the landmark image as a base point; a map image generation unit that generates a map image, which shows an imaged region and a non-imaged region of the imaging target organ, based on the virtual model in which the plurality of endoscopic images are assigned to respective portions by the mapping unit; and a display control unit that displays the map image generated by the map image generation unit on a monitor.

An image display method according to another aspect of the invention comprises: a storage step of storing imaging information including an endoscopic image of an imaging target organ in a storage unit; a connection relationship setting step of setting a connection relationship between a plurality of endoscopic images stored in the storage unit based on the imaging information; a landmark image detection step of detecting a landmark image including a predetermined anatomical landmark corresponding to the imaging target organ among the plurality of endoscopic images stored in the storage unit; a mapping step of assigning the detected landmark image to a landmark portion of a virtual model corresponding to the imaging target organ and assigning the plurality of endoscopic images stored in the storage unit to corresponding portions of the virtual model using the connection relationship set in the connection relationship setting step with the landmark image as a base point; a map image generation step of generating a map image, which shows an imaged region and a non-imaged region of the imaging target organ, based on the virtual model in which the plurality of endoscopic images are assigned to respective portions; and a display step of displaying the generated map image on a monitor, wherein the storage step, the connection relationship setting step, the landmark image detection step, the mapping step, the map image generation step, and the display step are executed by a computer.

A program according to still another aspect of the invention causes a computer to execute each of the steps described above.

According to the invention, it is possible to provide an image display device, an image display method, and a computer readable medium storing a program capable of accurately evaluating omission in imaging.

EXPLANATION OF REFERENCES

Figure 1:
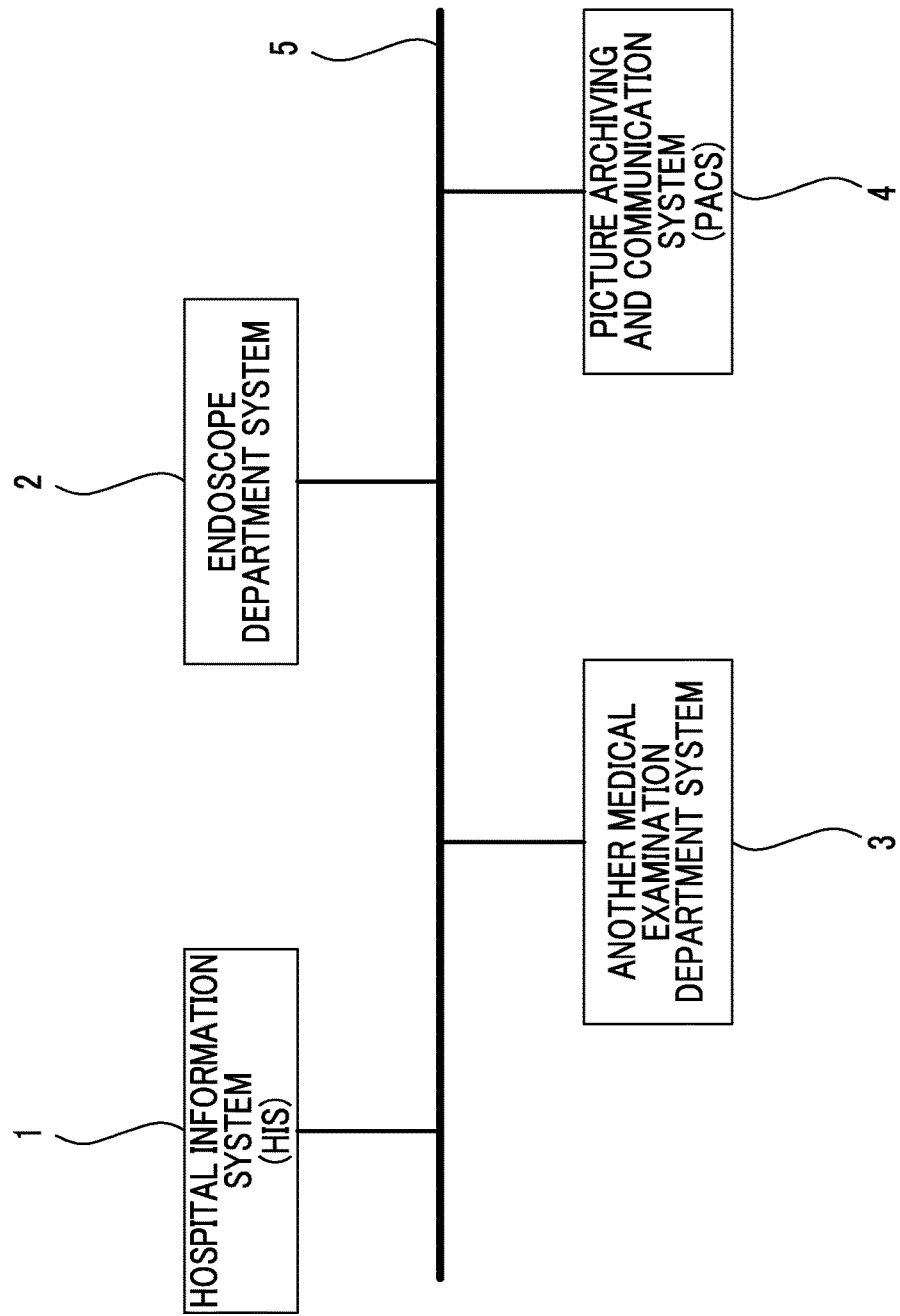
FIG. 1 is a block diagram of an example of a medical system illustrating an embodiment of the invention.

1: hospital information system
2: endoscope department system
3: another medical examination department system
4: picture archiving and communication system
5: in-hospital LAN
20: server computer
21: endoscope apparatus
22: computer
23: computer
24: in-department LAN
30: endoscope body
31: light source unit
32: processor unit
33: monitor
40: imaging unit
41: detection unit
42: operation unit
43: signal input and output unit
44: image processing unit
45: storage unit
46: transmission and reception unit
47: control unit
50: monitor
51: operation unit
52: transmission and reception unit
53: storage unit
54: control unit
60: connection relationship setting unit
61: landmark image detection unit
62: mapping unit
63: map image generation unit
64: display control unit
70: connection relationship setting unit
71: landmark image detection unit
72: mapping unit
73: map image generation unit
74: display control unit
DB: database
IMG1: endoscopic image
IMG2: endoscopic image
IMG3: endoscopic image
IMG4: endoscopic image
LM: pylorus (anatomical landmark)
R1: imaged region
R2: non-imaged region
R3-1: essential imaging region
R3-2: essential imaging region
R3-3: essential imaging region
Room1: endoscopic examination room
Room2: conference room

DESCRIPTION OF THE PREFERRED EMBODIMENTS

FIG. 1 shows a configuration example of a medical system illustrating an embodiment of the invention.

The medical system shown in FIG. 1 includes a hospital information system (HIS) 1, an endoscope department system 2, another medical examination department system 3 such as a radiology department system, and a picture archiving and communication system (PACS) 4. The HIS 1, the endoscope department system 2, another medical examination department system 3, and the PACS 4 can cooperate with each other through an in-hospital local area network (LAN) 5.

The HIS 1 is a comprehensive system including an electronic medical record system for storing an electronic medical record, in which medical examination information of a patient is recorded, and an ordering system for managing various kinds of order information, such as an endoscopic examination request. For example, in a case where an examination request is sent to an endoscope department from another medical examination department, if order information regarding the endoscopic examination request is issued, the issued order information is transmitted to the endoscope department system 2 through the HIS 1. The order information includes, for example, patient information, such as a patient name and a patient ID, and an examination type such as gastroscopic examination, esophageal endoscopic examination, and duodenoscopic examination.

The PACS 4 is a system for electronically storing, retrieving, and analyzing medical images captured by an endoscope apparatus or the like.

Figure 2:
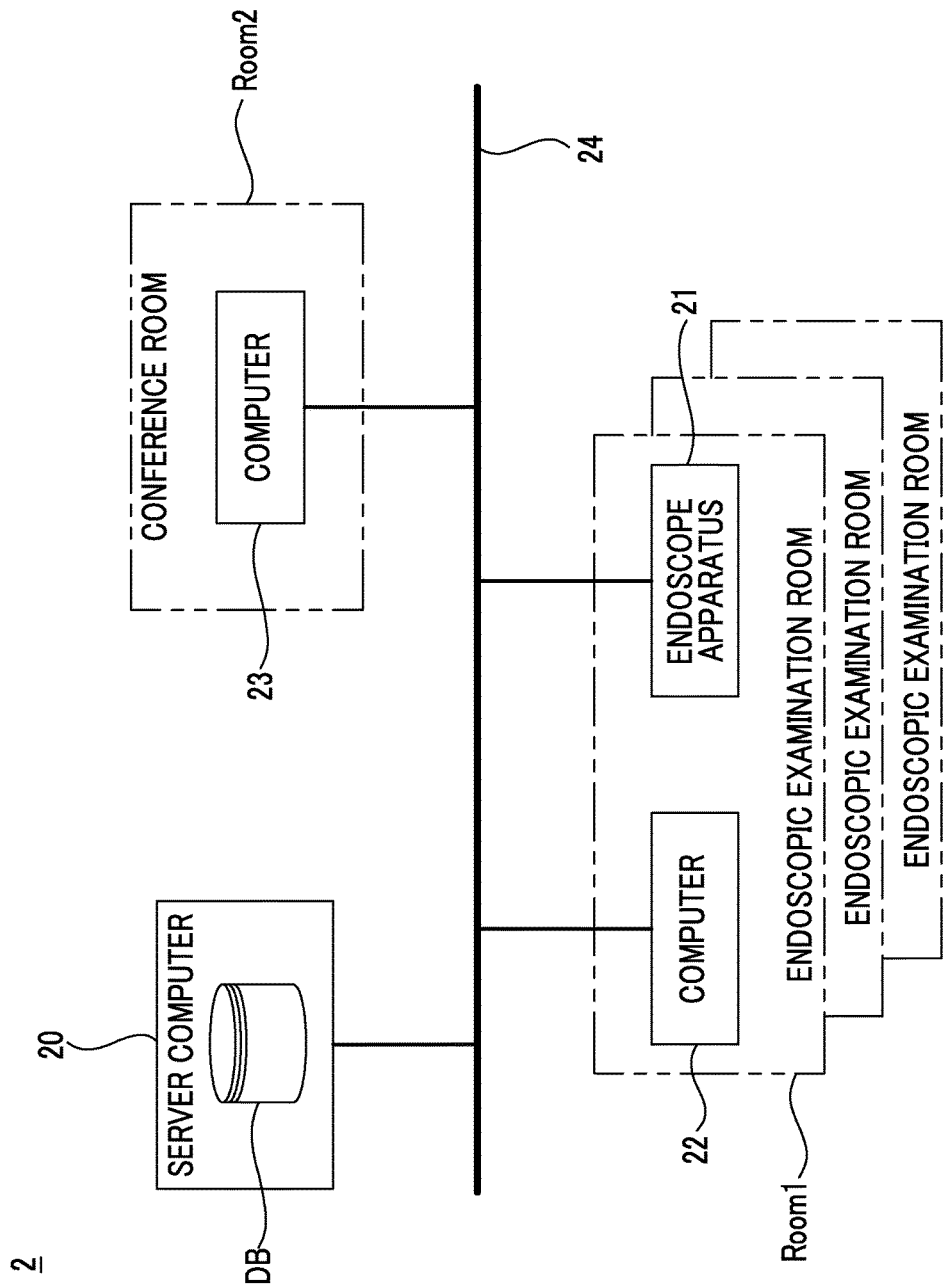
FIG. 2 is a block diagram of an example of an endoscope department system of the medical system shown in FIG. 1.

FIG. 2 shows an example of the endoscope department system 2.

In the endoscope department, a plurality of endoscopic examination rooms Room1 and a conference room Room2 are provided. In each of the endoscopic examination rooms Room1, an endoscope apparatus 21 and a computer 22 are installed. In the conference room Room2, a computer 23 is installed.

The endoscope department system 2 shown in FIG. 2 includes a server computer 20, the endoscope apparatus 21 and the computer 22 installed in each of the endoscopic examination rooms Room1, and the computer 23 installed in the conference room Room2. The server computer 20, the endoscope apparatus 21, the computer 22, and the computer 23 are connected to an in-department LAN 24, and the in-department LAN 24 is connected to the in-hospital LAN 5.

A database DB is built in the server computer 20, and various kinds of information including order information is stored in the database DB. The server computer 20 determines the assignment of endoscopic examinations to each of the endoscopic examination rooms Room1 based on the order information stored in the database DB, and transmits the order information to the endoscope apparatus 21 in each of the endoscopic examination rooms Room1 based on the determined assignment.

In the endoscopic examination room Room1, an endoscopic examination corresponding to the order information transmitted from the server computer 20 to the endoscope apparatus 21 is performed, and an image of an organ to be examined is captured by the endoscope apparatus 21. The image captured by the endoscope apparatus 21 is transmitted to the server computer 20 in a state in which the image is associated with the order information, and is stored in the server computer 20. The image stored in the server computer 20 is transmitted to the PACS 4 at an appropriate timing, and is stored in the PACS 4. The image captured by the endoscope apparatus 21 is also transmitted to the computer 22 installed in the same endoscopic examination room Room1 as the endoscope apparatus 21.

The image stored in the server computer 20 or the PACS 4 can be searched and used from the computer 23 installed in the conference room Room2 using, for example, patient information, such as a patient name and a patient ID included in the associated order information, as a search key.

The computer 22 installed in the endoscopic examination room Room1 and the computer 23 installed in the conference room Room2 operate according to programs installed in these computers, thereby generating a map image showing an imaged region and a non-imaged region of the imaging target organ from the image captured by the endoscope apparatus 21. In addition, the computer 22 installed in the endoscopic examination room Room1 and the computer 23 installed in the conference room Room2 function as image display devices that display the generated map image.

Figure 3:
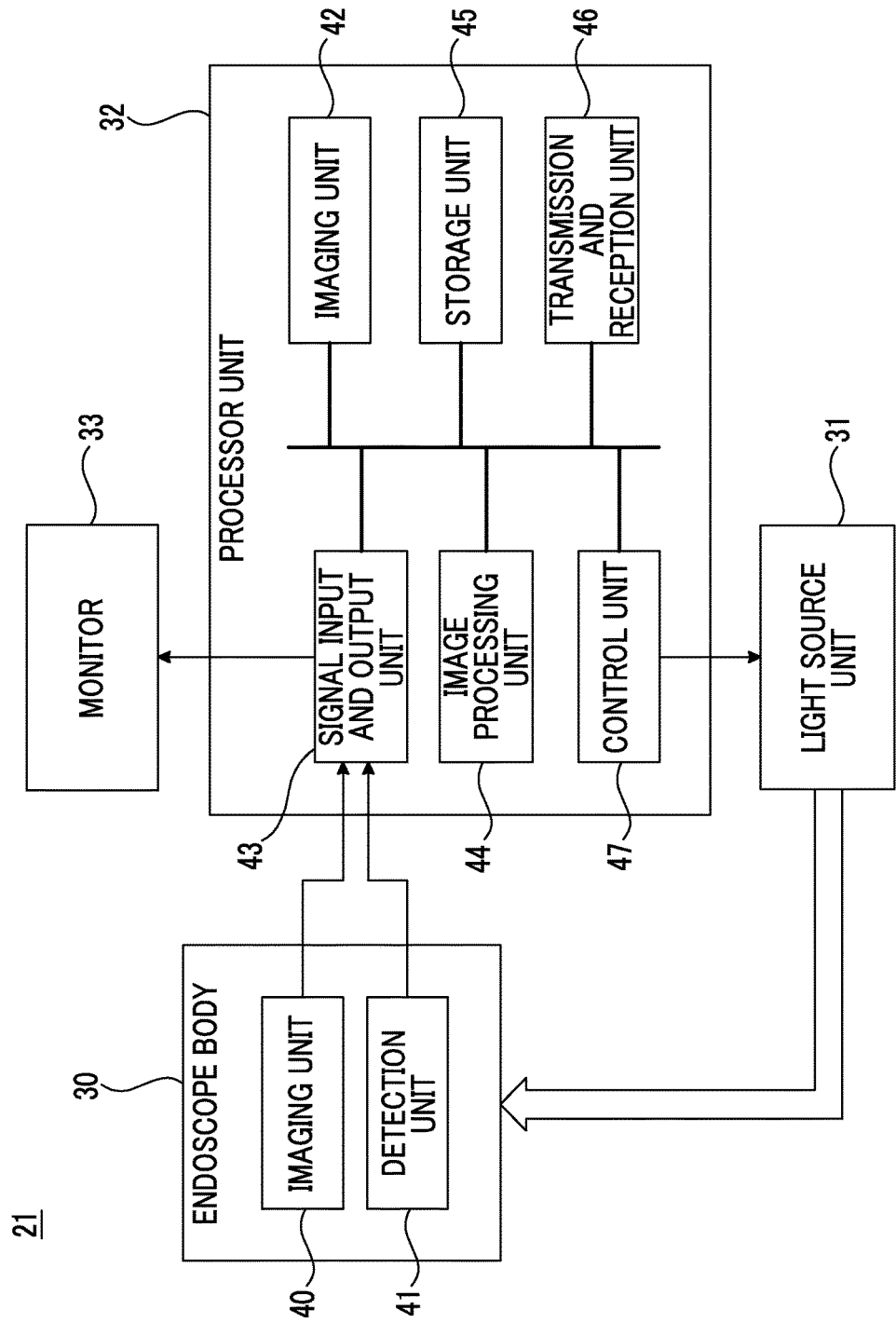
FIG. 3 is a block diagram of an endoscope apparatus included in the endoscope department system shown in FIG. 2.

FIG. 3 shows a configuration example of the endoscope apparatus 21.

As shown in FIG. 3, the endoscope apparatus 21 includes an endoscope body 30, a light source unit 31, a processor unit 32, and a monitor 33.

The endoscope body 30 has an imaging unit 40 including an imaging element. The imaging unit 40 is provided in a distal end portion of an insertion part inserted into the body of the patient, and images an examination target organ of the patient.

In this example, the endoscope body 30 has a detection unit 41 that detects at least one imaging condition of the position, the posture, or the subject distance of the distal end portion of the insertion part in which the imaging unit 40 is provided.

The position of the distal end portion of the insertion part can be detected as a movement distance obtained by integrating the acceleration twice using an acceleration sensor, for example. The posture of the distal end portion of the insertion part can be detected as a rotation angle obtained by integrating the angular rate once using an angular rate sensor, for example. The subject distance can be detected using a distance sensor, such as an infrared distance sensor, for example. The detection unit 41 includes the above-described sensors corresponding to the imaging condition to be detected, and is provided in the distal end portion of the insertion part.

The light source unit 31 generates illumination light for illuminating an examination target organ captured by the imaging unit 40 of the endoscope body 30. The illumination light generated by the light source unit 31 is guided to the distal end portion of the insertion part of the endoscope body 30 through a light guide, and is emitted toward the subject from the distal end portion.

The processor unit 32 includes an operation unit 42 for receiving various operation inputs, a signal input and output unit 43, an image processing unit 44, a storage unit 45, a transmission and reception unit 46, and a control unit 47 that controls the operation unit 42, the signal input and output unit 43, the image processing unit 44, the storage unit 45, and the transmission and reception unit 46.

An imaging signal output from the imaging unit 40 of the endoscope body 30 and a detection signal output from the detection unit 41 of the endoscope body 30 are input to the signal input and output unit 43. The imaging signals input to the signal input and output unit 43 are transmitted to the image processing unit 44, and the image processing unit 44 performs various kinds of signal processing on the imaging signals to convert the imaging signals into image data. The image data obtained by the conversion of the image processing unit 44 is output toward the monitor 33 from the signal input and output unit 43, and is displayed on the monitor 33 as a real-time observation image.

In addition, the image data obtained by the conversion of the image processing unit 44 is stored in the storage unit 45 as a still image or a motion picture. Whether the image data is stored as a still image or as a motion picture is selected based on the operator's operation input to the operation unit 42.

In a case where image data is stored as a still image, not only a still image captured at a timing at which the imaging instruction of the operator is input to the endoscope body 30 but also a plurality of still images that are automatically captured at predetermined time intervals by the control unit 47 are stored in the storage unit 45. The above-described still images that are intermittently captured are hereinafter referred to as interval images. The imaging interval of interval images can be appropriately set based on the operator's operation input to the operation unit 42.

The interval images are stored in the storage unit 45 so as to be associated with the imaging order. The imaging order is represented by imaging time, for example. In this example, at least one imaging condition of the position, the posture, or the subject distance of the distal end portion of the insertion part, which are detected by the detection unit 41 of the endoscope body 30, is input to the signal input and output unit 43 as a detection signal, and the interval image is stored in the storage unit 45 so as to be associated with the imaging condition at the time of imaging.

A plurality of interval images stored in the storage unit 45 and the imaging order and the imaging condition, which are associated with each of the interval images, are transmitted from the transmission and reception unit 46 to the server computer 20, as imaging information, at a timing at which the examination ends, for example. Each time an interval image is captured, the interval image and the imaging order and the imaging condition associated with the interval image are sequentially transmitted from the transmission and reception unit 46 to the computer 22, which is installed in the same room as the endoscope apparatus 21, imaging information.

In a case where image data is stored as a motion picture, the motion picture is stored in the storage unit 45 in a state in which the imaging order is associated with each of frame images (still images) forming the motion picture. The imaging order is represented by a time code incident the position of each frame image in the motion picture, for example. In this example, the motion picture is stored in the storage unit 45 in a state in which the imaging condition at the time of imaging is associated with each frame image.

The motion picture stored in the storage unit 45 and the imaging order and the imaging condition, which are associated with each frame image forming the motion picture, are transmitted from the transmission and reception unit 46 to the server computer 20, as imaging information, at a timing at which the examination ends, for example. Each time a frame image is added to a motion picture, the frame image and the imaging order and the imaging condition associated with the frame image are sequentially transmitted from the transmission and reception unit 46 to the computer 22, which is installed in the same room as the endoscope apparatus 21, imaging information.

Figure 4:
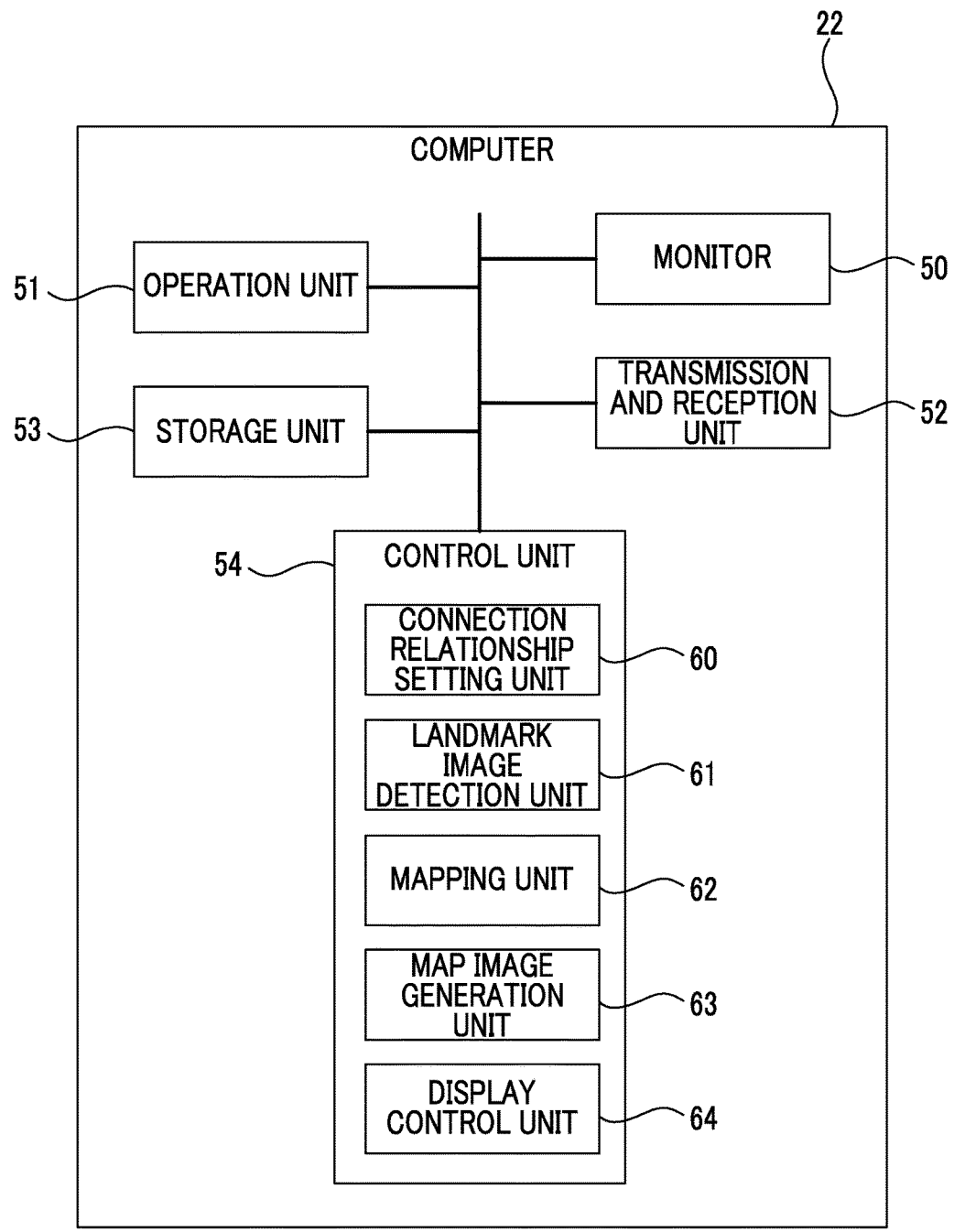
FIG. 4 is a block diagram of an example of a computer as an image display device included in the endoscope department system shown in FIG. 2.

FIG. 4 shows a configuration example of the computer 22.

As shown in FIG. 4, the computer 22 includes a monitor 50 for displaying an image or the like, an operation unit 51 for receiving various operation inputs, a transmission and reception unit 52 for receiving imaging information sequentially transmitted from the endoscope apparatus 21, a storage unit 53, and a control unit 54 that controls the monitor 50, the operation unit 51, the transmission and reception unit 52, and the storage unit 53.

The storage unit 53 is configured to include a storage medium, such as a hard disk, and stores a program executed by the control unit 54. The control unit 54 is configured to include one or more processors for executing a program and a memory forming a work area in the case of executing a program, and the following functions are provided by the control unit 54 that executes the program.

First, the control unit 54 stores the imaging information received by the transmission and reception unit 52 in the storage unit 53.

In a case where image data is recorded as a still image in the endoscope apparatus 21, an interval image and the imaging order and the imaging condition associated with the interval image are sequentially transmitted to the computer 22 as imaging information. In this case, the interval image received by the transmission and reception unit 52 is stored in the storage unit 53, as an endoscopic image for map image generation, in a state in which the interval image is associated with the imaging order and the imaging condition.

On the other hand, in a case where image data is recorded as a motion picture in the endoscope apparatus 21, a frame image and the imaging order and the imaging condition associated with the frame image are sequentially transmitted to the computer 22 as imaging information. In this case, a frame image received at a timing defined by a predetermined time interval, among frame images received by the transmission and reception unit 52, is extracted as one still image. Then, the extracted frame image is stored in the storage unit 53, as an endoscopic image for map image generation, in a state in which the extracted frame image is associated with the imaging order and the imaging condition. The time interval at which a frame image is extracted can be appropriately set based on the operator's operation input to the operation unit 51.

The control unit 54 functions as a connection relationship setting unit 60, a landmark image detection unit 61, a mapping unit 62, a map image generation unit 63, and a display control unit 64.

The connection relationship setting unit 60 sets the connection relationship between a plurality of endoscopic images stored in the storage unit 53. The connection relationship between endoscopic images can be set using the imaging order associated with the endoscopic images, for example. Since the interval image and the frame image regarded as endoscopic images are captured at predetermined time intervals or are extracted from the motion picture at predetermined time intervals, the imaging ranges of endoscopic images in the front and back relationship in the imaging order are at least close to each other. Therefore, the endoscopic images in the front and back relationship in the imaging order can be connected to each other.

The connection relationship between endoscopic images can be set using a feature pattern appearing in the image. Examples of the feature pattern include a color pattern, such as a blood vessel and rubor, and a structural pattern, such as wrinkles and rashes, and endoscopic images having a common feature pattern can be connected to each other. For example, the feature pattern can be extracted from the endoscopic image using an image analysis method, such as color extraction and edge extraction, and the common feature pattern can be detected using a known image matching method, such as feature-based matching and region-based matching.

In addition, the connection relationship between endoscopic images can be set using the imaging condition (position, posture, and subject distance) associated with the endoscopic images. Since the imaging range of each endoscopic image can be known based on the position, posture, and subject distance of the distal end portion of the insertion part of the endoscope body 30 in which the imaging unit 40 is provided, endoscopic images with overlapping or adjacent imaging ranges can be connected to each other.

By setting the connection relationship between endoscopic images by combining two or more of the imaging order, the feature pattern, and the imaging condition described above, it is possible to set the connection relationship more accurately and efficiently. For example, in the case of connecting endoscopic images having a common feature pattern to each other, it is preferable to deform the endoscopic images so that the common feature patterns match each other. If the endoscopic images are deformed based on at least one imaging condition of the position, the posture, or the subject distance, it is possible to efficiently search for the amount of deformation of each of the endoscopic images whose common feature patterns match each other. By matching the common feature patterns, it is possible to set the connection relationship more accurately.

The landmark image detection unit 61 detects a landmark image including a predetermined anatomical landmark corresponding to the imaging target organ, among a plurality of endoscopic images stored in the storage unit 53.

Here, the anatomical landmark refers to a part that is necessarily present in the imaging target organ and shows a characteristic shape. In the case of a stomach, a cardia, a pylorus, and a gastric horn can be exemplified. In the case of an esophagus, a pharynx and a cardia can be exemplified. In the case of a duodenum, a ball head and a nipple can be exemplified. For example, the anatomical landmark can be detected using a known image matching method, such as feature-based matching and region-based matching.

The mapping unit 62 assigns the landmark image detected by the landmark image detection unit 61 to a landmark portion of a virtual model corresponding to the imaging target organ. With the landmark image assigned to the landmark portion as a base point, the mapping unit 62 assigns a plurality of endoscopic images stored in the storage unit 53 to corresponding portions of the virtual model using the connection relationship set by the connection relationship setting unit 60. The virtual model may be a three-dimensional model of the imaging target organ, or may be a two-dimensional model obtained by developing the three-dimensional model in a plane.

The map image generation unit 63 generates a map image, which shows an imaged region and a non-imaged region of the imaging target organ, based on the virtual model in which a plurality of endoscopic images are assigned to respective portions by the mapping unit 62.

The display control unit 64 displays the map image generated by the map image generation unit 63 on the monitor 50.

The imaging target organ and the virtual model corresponding to the imaging target organ are specified based on the operator's operation input to the operation unit 51. In addition, order information may be transmitted from the server computer 20 to the computer 22 or order information may be transmitted from the endoscope apparatus 21 to the computer 22, so that the imaging target organ and the virtual model corresponding to the imaging target organ are automatically specified by the control unit 54 based on the examination type included in the order information.

Hereinafter, the processing of the computer 22 will be described by taking the gastroscopic examination as an example. In the gastroscopic examination, typically, the insertion part is inserted into the body of the patient until the distal end portion of the insertion part of the endoscope body 30 is disposed near the pylorus of the stomach, and then the insertion part is gradually withdrawn. Then, while the insertion part is being gradually withdrawn, the posture of the distal end portion of the insertion part is variously changed to image each portion of the stomach. As anatomical landmarks of the stomach, a cardia, a pylorus, and a gastric angle can be exemplified. However, according to the examination method described above, an image including the pylorus is captured by the endoscope apparatus 21 at a relatively early stage from the start of the examination. In this example, therefore, it is assumed that the pylorus is set as an anatomical landmark.

Figure 5:
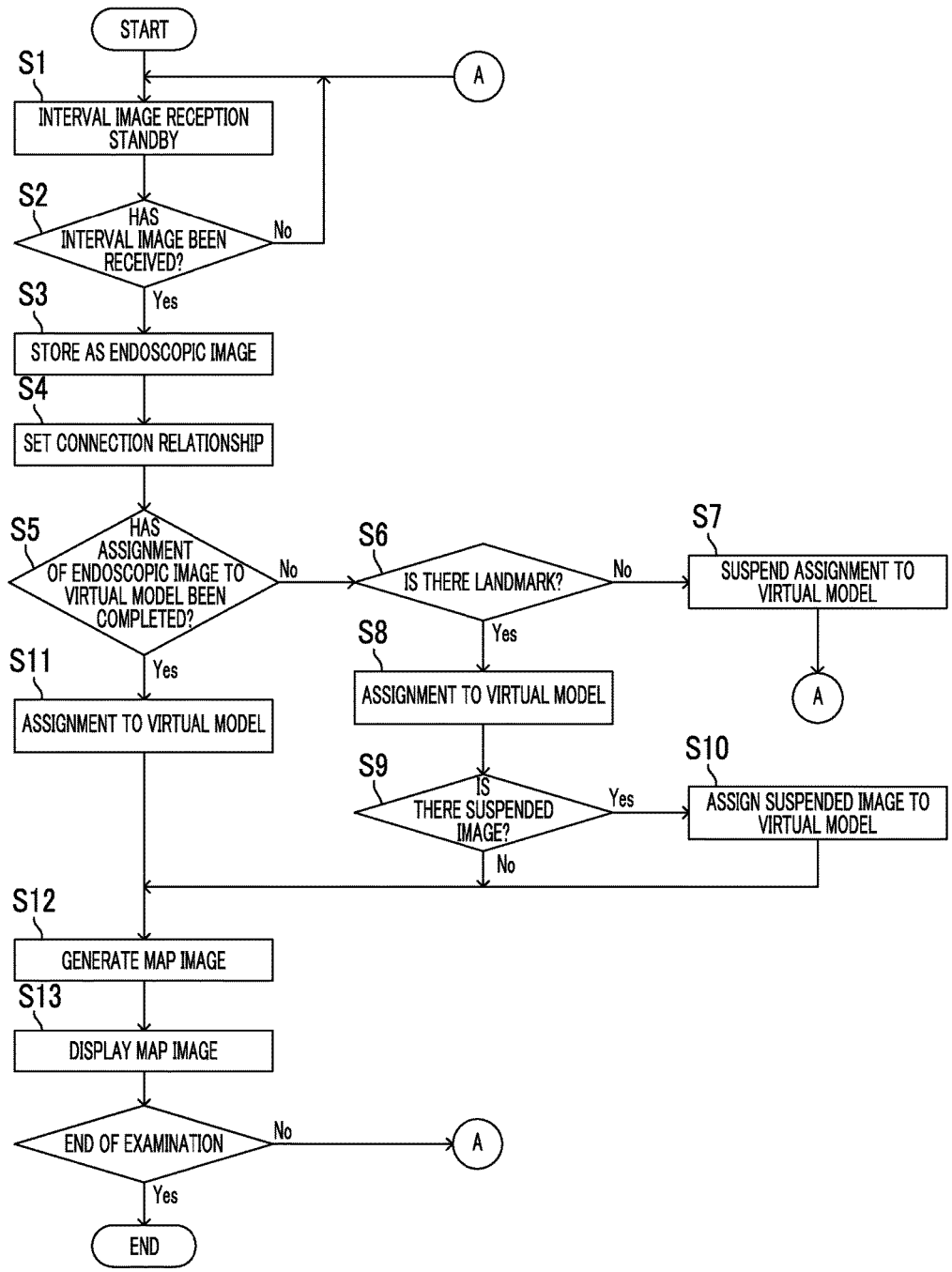
FIG. 5 is a flowchart of an example of processing executed by the computer shown in FIG. 4.

FIG. 5 shows an example of the processing of the computer 22.

FIG. 5 shows the processing of the computer 22 in a case where image data is recorded as a still image in the endoscope apparatus 21.

First, the control unit 54 of the computer 22 is in a standby state for receiving an interval image (step S1). When an interval image is received by the transmission and reception unit 52 (Yes in step S2), the received interval image is stored in the storage unit 53 as an endoscopic image for map image generation (step S3).

Then, the control unit 54 (connection relationship setting unit 60) sets the connection relationship between the endoscopic image stored in the storage unit 53 in step S3 and the endoscopic image already stored in the storage unit 53 (step S4).

Then, the control unit 54 determines whether or not one or more endoscopic images are already assigned to the virtual model (step S5).

In a case where no endoscopic image is assigned to the virtual model (No in step S5), the control unit 54 (landmark image detection unit 61) determines whether or not an anatomical landmark is included in the endoscopic image stored in the storage unit 53 in step S3 (step S6).

In a case where no anatomical landmark is included in the endoscopic image (No in step S6), the control unit 54 suspends the assignment of the endoscopic image to the virtual model (step S7), and returns to step S1.

On the other hand, in a case where an anatomical landmark is included in the endoscopic image (Yes in step S6), the control unit 54 (mapping unit 62) assigns the endoscopic image (landmark image) to the landmark portion of the virtual model (step S8).

Then, the control unit 54 determines whether or not there is an endoscopic image whose assignment to the virtual model has been suspended in step S7 (step S9). In a case where there is a suspended endoscopic image (Yes in step S9), the control unit 54 (mapping unit 62) assigns the suspended endoscopic image to the corresponding portion of the virtual model using the connection relationship set in step S4 with the landmark image assigned to the landmark portion as a base point (step S10).

Figure 6:
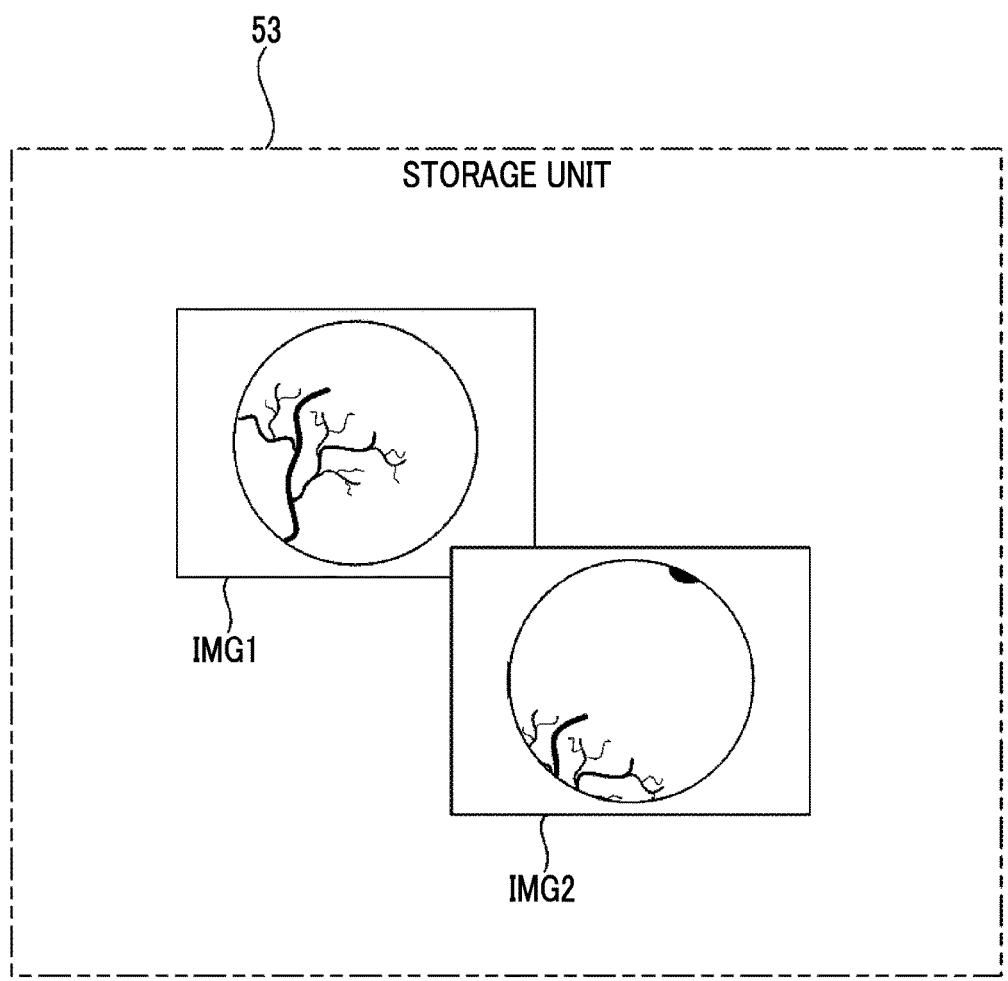
FIG. 6 is a schematic diagram illustrating the processing shown in FIG. 5.
Figure 7:
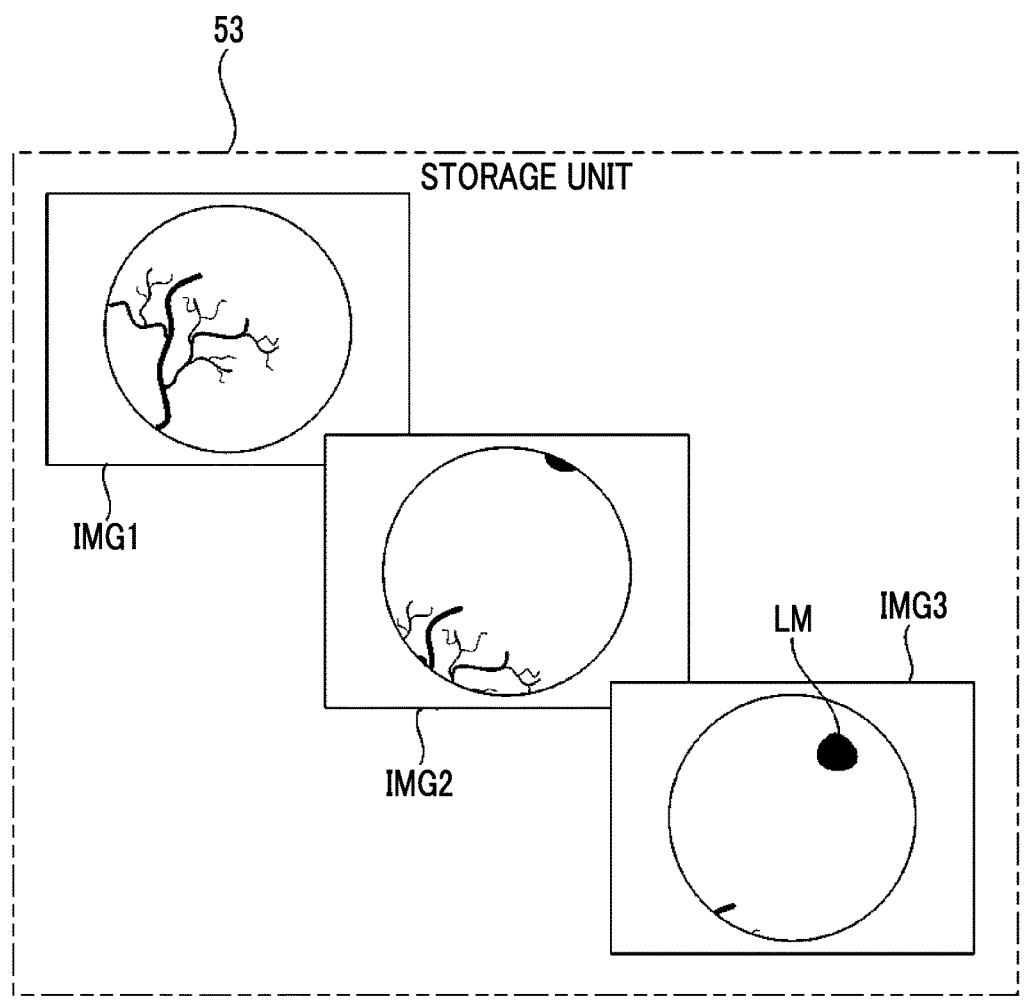
FIG. 7 is a schematic diagram illustrating the processing shown in FIG. 5.
Figure 8:
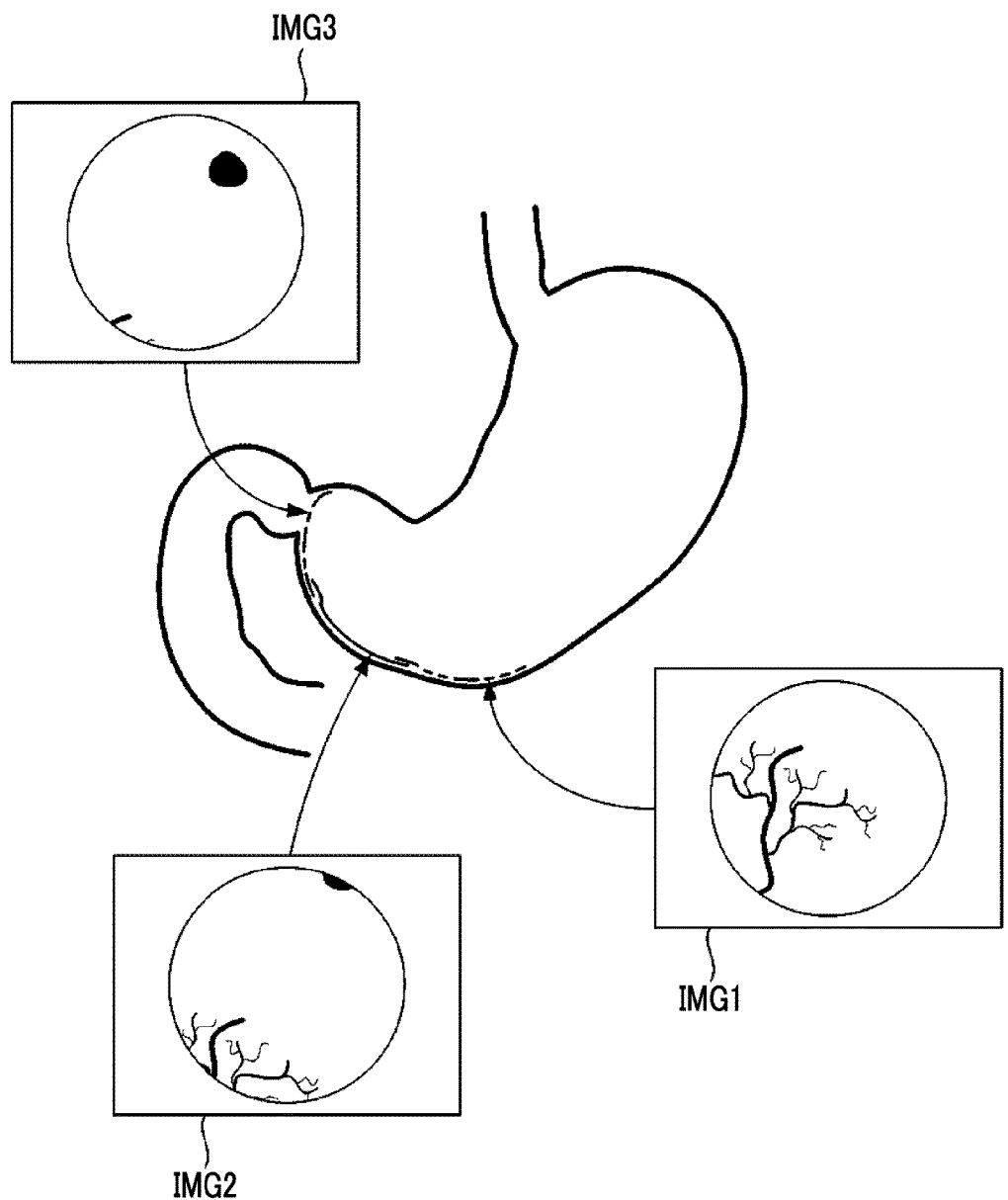
FIG. 8 is a schematic diagram illustrating the processing shown in FIG. 5.

FIGS. 6 to 8 schematically show the processing from step S1 to step S10.

First, as shown in FIG. 6, an endoscopic image IMG1 and an endoscopic image IMG2 are stored in the storage unit 53. The serial number subsequent to the reference numeral "IMG" attached to the endoscopic image indicates the imaging order of the endoscopic image. The endoscopic image IMG1 and the endoscopic image IMG2 do not includes a pylorus as an anatomical landmark, and the assignment of the endoscopic image IMG1 and the endoscopic image IMG2 to the virtual model is suspended.

Then, as shown in FIG. 7, an endoscopic image IMG3 is stored in the storage unit 53. The endoscopic image IMG3 includes a pylorus LM, and the endoscopic image IMG3 is detected as a landmark image.

Then, as shown in FIG. 8, the endoscopic image IMG3 detected as a landmark image is assigned to the pylorus portion that is a landmark portion of the virtual model. Then, with the endoscopic image IMG3 assigned to the pylorus portion as a base point, the endoscopic image IMG2 captured immediately before the endoscopic image IMG3 is assigned to a portion adjacent to the pylorus portion to which the endoscopic image IMG3 is assigned. Then, the endoscopic image IMG1 captured immediately before the endoscopic image IMG2 is assigned to a portion adjacent to the portion to which the endoscopic image IMG2 is assigned.

Referring back to FIG. 5, after assigning the landmark image and the suspended endoscopic image to the corresponding portion of the virtual model, the control unit 54 (map image generation unit 63) generates a map image showing an imaged region and a non-imaged region of the imaging target organ based on the virtual model in which the endoscopic image is assigned to each portion at that point in time (step S12). Then, the control unit 54 (display control unit 64) displays the map image generated in step S12 on the monitor 50 (step S13).

Figure 9:
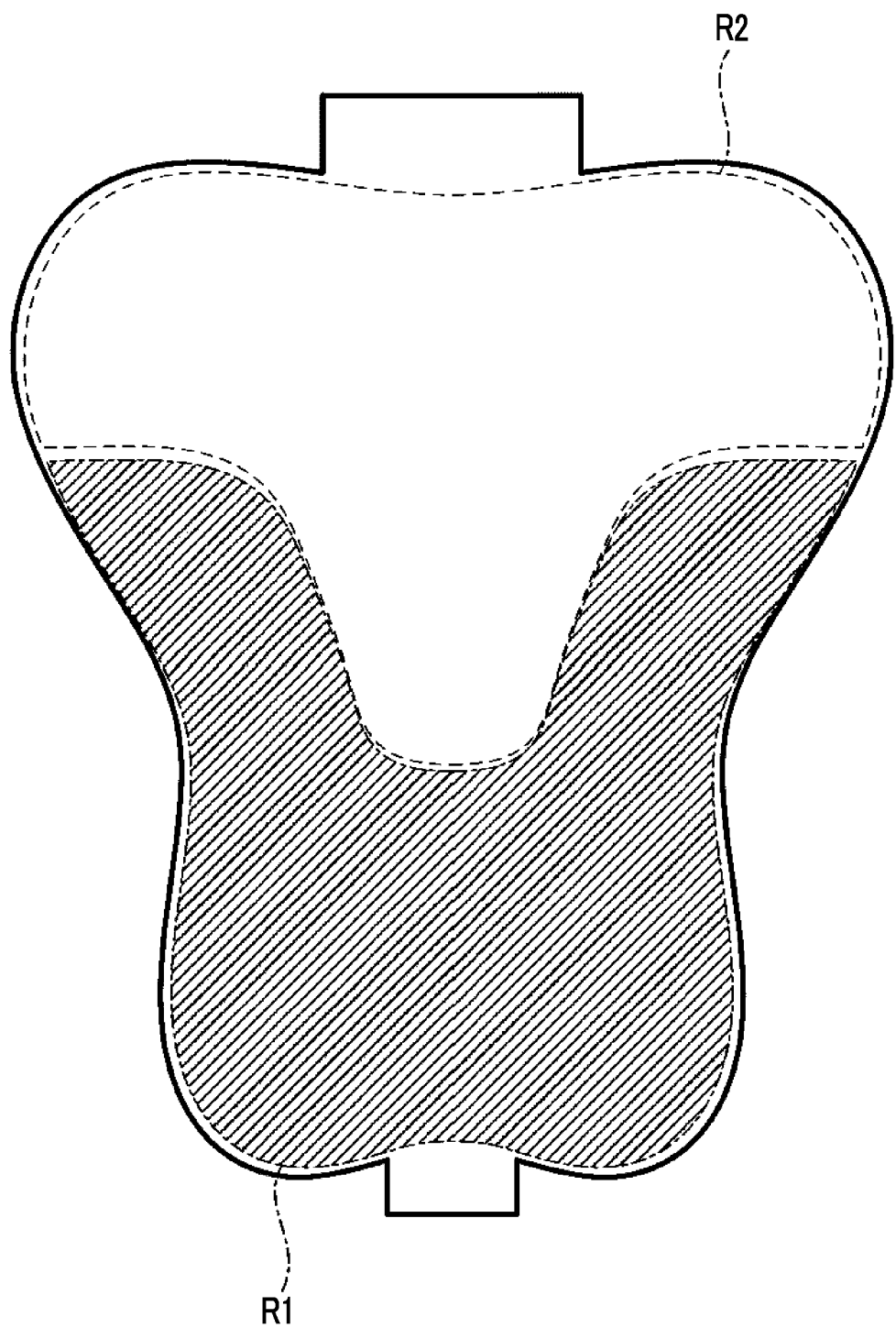
FIG. 9 is a schematic diagram of a map image generated by the computer shown in FIG. 4 and a display example thereof.

FIG. 9 shows an example of a map image.

The map image shown in FIG. 9 is generated based on the virtual model in which the endoscopic images IMG1 to IMG3 shown in FIG. 8 are assigned to respective portions. The map image is formed by being displayed in a state in which an imaged region and a non-imaged region can be distinguished on the outline view obtained by developing the stomach, which is an imaging target organ, in a plane.

An imaged region R1 is a region to which the endoscopic images IMG1 to IMG3 are assigned in the virtual model. In the shown example, the imaged region R1 is displayed with diagonal lines. On the other hand, a non-imaged region R2 is a region to which no endoscopic image is assigned in the virtual model. In the shown example, the non-imaged region R2 is displayed as a blank. That is, the non-imaged region R2 is displayed in the background color of the display screen of the monitor 50.

The display mode of each of the imaged region R1 and the non-imaged region R2 is an example, and is not particularly limited as long as these can be distinguished. For example, the imaged region R1 may be displayed by pasting the endoscopic images IMG1 to IMG3 as textures.

Referring back to FIG. 5, the following processing of the computer 22 will be described assuming that the endoscopic examination is continued.

After the map image generated based on the virtual model in which the endoscopic images IMG1 to IMG3 are assigned to respective portions is displayed on the monitor 50, the control unit 54 returns to step S1 to shift to the standby state for receiving an interval image (step S1). In a case where an interval image is received by the transmission and reception unit 52 (Yes in step S2), the received interval image is stored in the storage unit 53 as an endoscopic image IMG4 for map image generation (step S3), and the connection relationship between the endoscopic image IMG4 and the endoscopic images IMG1 to IMG3 already stored in the storage unit 53 is set (step S4).

Then, the control unit 54 determines whether or not one or more endoscopic images are already assigned to the virtual model (step S5). Here, since the endoscopic images IMG1 to IMG3 are already assigned to respective portions of the virtual model, the control unit 54 (mapping unit 62) assigns the endoscopic image IMG4 to the corresponding portion of the virtual model using the connection relationship set in step S4 (step S11).

Then, the control unit 54 (map image generation unit 63) generates a new map image based on the virtual model in which the endoscopic images IMG1 to IMG4 are assigned to respective portions (step S12). Then, the control unit 54 (display control unit 64) displays the new map image generated in step S12 on the monitor 50 (step S13).

Thereafter, the control unit 54 repeats the processing of steps S1 to S5 and steps S11 to S13 until the endoscopic examination ends, so that an interval image is stored in the storage unit 53 as an endoscopic image each time the interval image sequentially transmitted from the endoscope apparatus 21 is received by the transmission and reception unit 52, a map image is generated each time an endoscopic image is stored in the storage unit 53, and the generated map image is displayed on the monitor 50 each time a map image is generated. As a result, the map image displayed on the monitor 50 is changed in accordance with the progress of the endoscopic examination.

In the example shown in FIG. 5, after a landmark image is detected and once a map image is generated, a new map image is generated each time a new endoscopic image is stored in the storage unit 53. However, a new map image can be generated each time a plurality of (for example, two) new endoscopic images are stored in the storage unit 53. The number of new still image stored until a map image is generated may be fixed, or may be changeable based on, for example, the operator's operation input to the operation unit 51.

Next, the processing of the computer 22 in a case where image data is recorded as a motion picture in the endoscope apparatus 21 will be described with reference to FIGS. 10 and 11.

Figure 10:
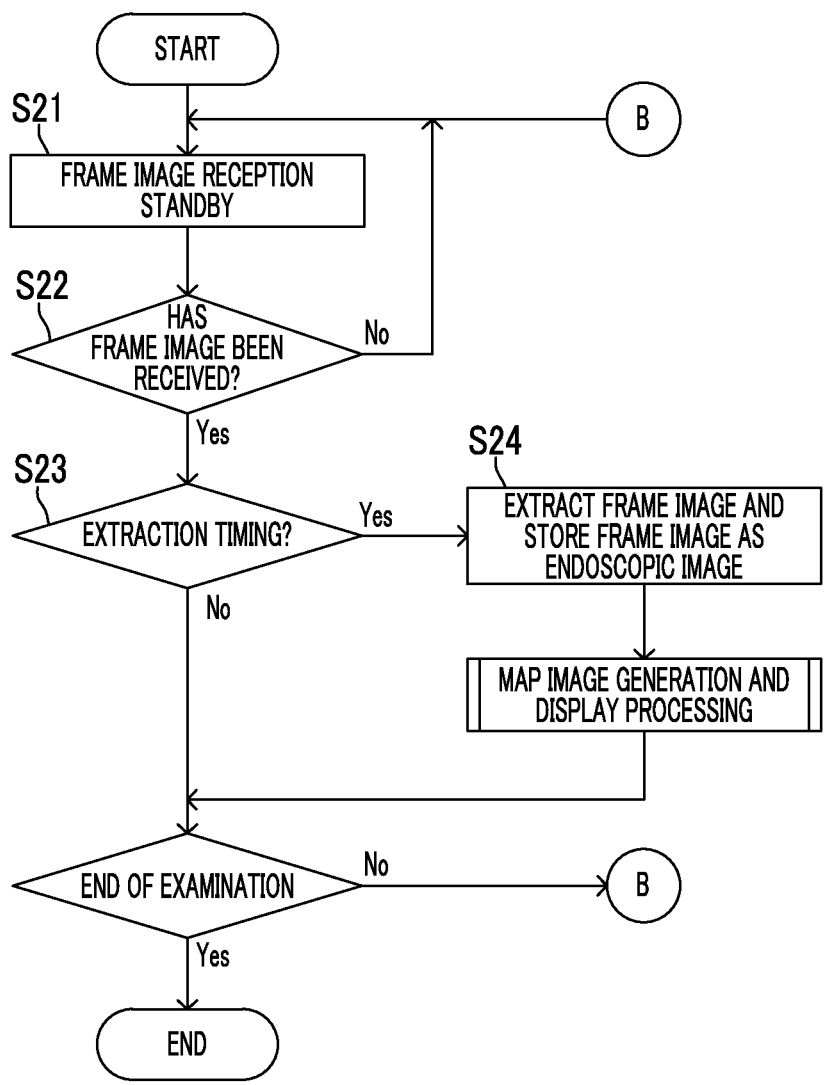
FIG. 10 is a flowchart of the main routine of another example of the processing executed by the computer shown in FIG. 4.

First, as shown in FIG. 10, the control unit 54 of the computer 22 is in a standby state for receiving a frame image forming a motion picture (step S21). In a case where a frame image is received by the transmission and reception unit 52 (Yes in step S22) and this is a timing defined by a predetermined time interval (Yes in step S23), the received frame image is extracted as one still image, and the extracted frame image is stored in the storage unit 53 as an endoscopic image for map image generation (step S24). Then, the control unit 54 proceeds to processing for generating and displaying a map image as a subroutine.

Figure 11:
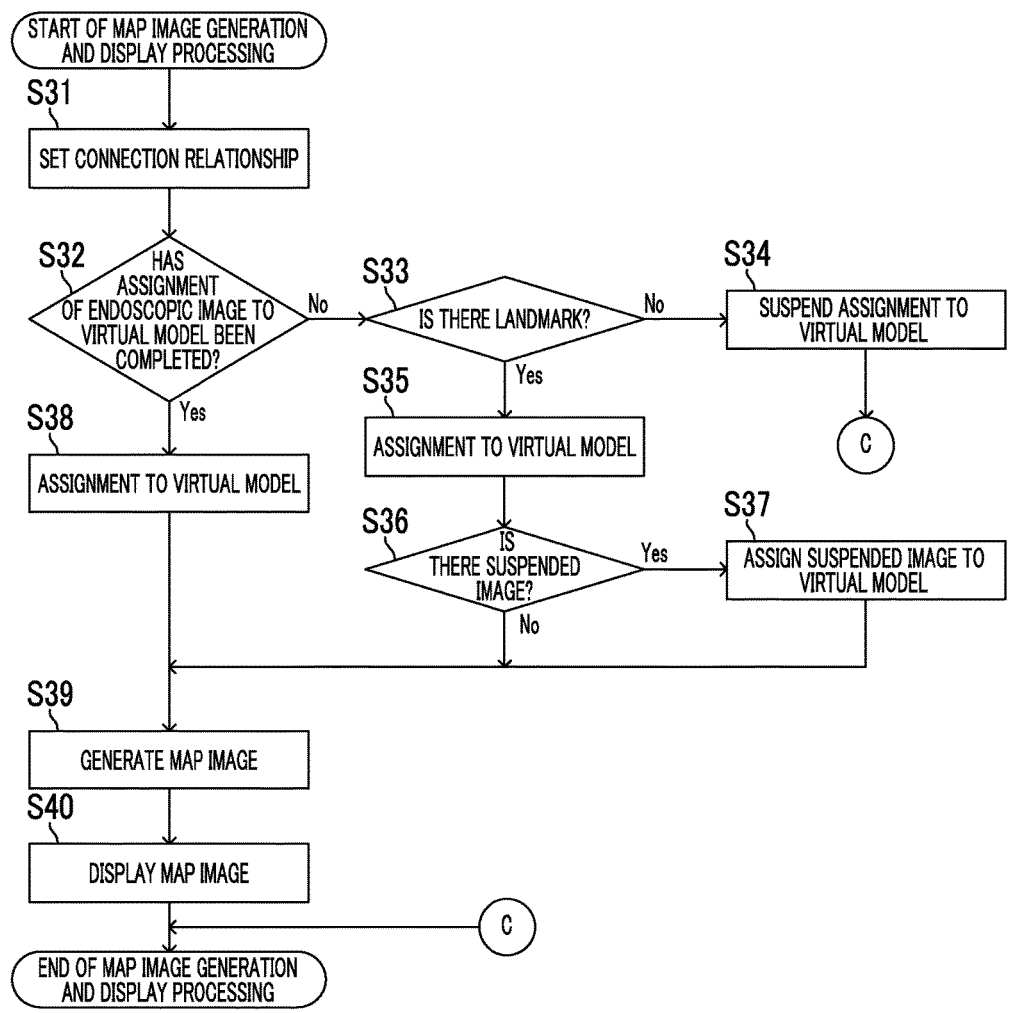
FIG. 11 is a flowchart of the subroutine of the processing shown in FIG. 10.

As shown in FIG. 11, the control unit 54 (connection relationship setting unit 60) that has proceeded to the processing for generating and displaying a map image sets the connection relationship between the endoscopic image stored in the storage unit 53 in step S24 and the endoscopic image already stored in the storage unit 53 (step S31).

Then, the control unit 54 determines whether or not one or more endoscopic images are already assigned to the virtual model (step S32).

In a case where no endoscopic image is assigned to the virtual model (No in step S32), the control unit 54 (landmark image detection unit 61) determines whether or not an anatomical landmark is included in the endoscopic image stored in the storage unit 53 in step S24 (step S33).

In a case where no anatomical landmark is included in the endoscopic image (No in step S33), the control unit 54 (mapping unit 62) suspends the assignment of the endoscopic image to the virtual model (step S34), and returns to the main routine shown in FIG. 10.

On the other hand, in a case where an anatomical landmark is included in the endoscopic image (Yes in step S33), the control unit 54 (mapping unit 62) assigns the endoscopic image (landmark image) to the landmark portion of the virtual model (step S35).

Then, the control unit 54 determines whether or not there is an endoscopic image whose assignment to the virtual model has been suspended in step S34 (step S36). In a case where there is a suspended endoscopic image (Yes in step S36), the control unit 54 (mapping unit 62) assigns the suspended endoscopic image to the corresponding portion of the virtual model using the connection relationship set in step S31 with the landmark image assigned to the landmark portion as a base point (step S37).

After assigning the landmark image and the suspended endoscopic image to the corresponding portion of the virtual model, the control unit 54 (map image generation unit 63) generates a map image showing an imaged region and a non-imaged region of the imaging target organ based on the virtual model in which the endoscopic image is assigned to each portion at that point in time (step S39). Then, the control unit 54 (display control unit 64) displays the map image generated in step S39 on the monitor 50 (step S40), and returns to the main routine shown in FIG. 10.

On the other hand, in a case where one or more endoscopic images are already assigned to the virtual model in the determination of step S32 (Yes in step S32), the control unit 54 (mapping unit 62) assigns the endoscopic image stored in the storage unit 53 in step S24 to the corresponding portion of the virtual model using the connection relationship set in step S31 (step S38).

Then, the control unit 54 (map image generation unit 63) generates a map image based on the virtual model in which the endoscopic image is assigned to each portion (step S39). Then, the control unit 54 (display control unit 64) displays the map image generated in step S39 on the monitor 50 (step S40), and returns to the main routine shown in FIG. 10.

Thus, the control unit 54 extracts a frame image from the motion picture at each extraction timing, stores the extracted frame image in the storage unit 53 as an endoscopic image, generates a map image each time an endoscopic image is stored in the storage unit 53, and displays the generated map image on the monitor 50 each time a map image is generated. As a result, the map image displayed on the monitor 50 is changed in accordance with the progress of the endoscopic examination.

Even in a case where an endoscopic image for map image generation is intermittently extracted from the motion picture, after a landmark image is detected and once a map image is generated, a new map image can be generated each time a new endoscopic image is stored in the storage unit 53 as described above, or a new map image can be generated each time a plurality of new endoscopic images are stored in the storage unit 53.

According to the computer 22 as an image display device described above and an image display method executed by the computer 22, since other endoscopic images are assigned to corresponding portions of the virtual model with a landmark image, which includes an anatomical landmark assigned to the landmark portion of the virtual model, as a base point, the accuracy of the position of each endoscopic image on the virtual model is improved. Therefore, the accuracy of region designation for each of the imaged region and the non-imaged region on the map image generated from the virtual model, in which a plurality of endoscopic images are assigned to respective portions, is also improved. As a result, it is possible to accurately evaluate omission in imaging.

In addition, according to the computer 22 as an image display device described above and the image display method executed by the computer 22, since the map image displayed on the monitor 50 is changed in accordance with the progress of the endoscopic examination, the operator can check whether or not there is omission in imaging while advancing the examination. As a result, it is possible to improve the efficiency of the endoscopic examination.

Figure 12:
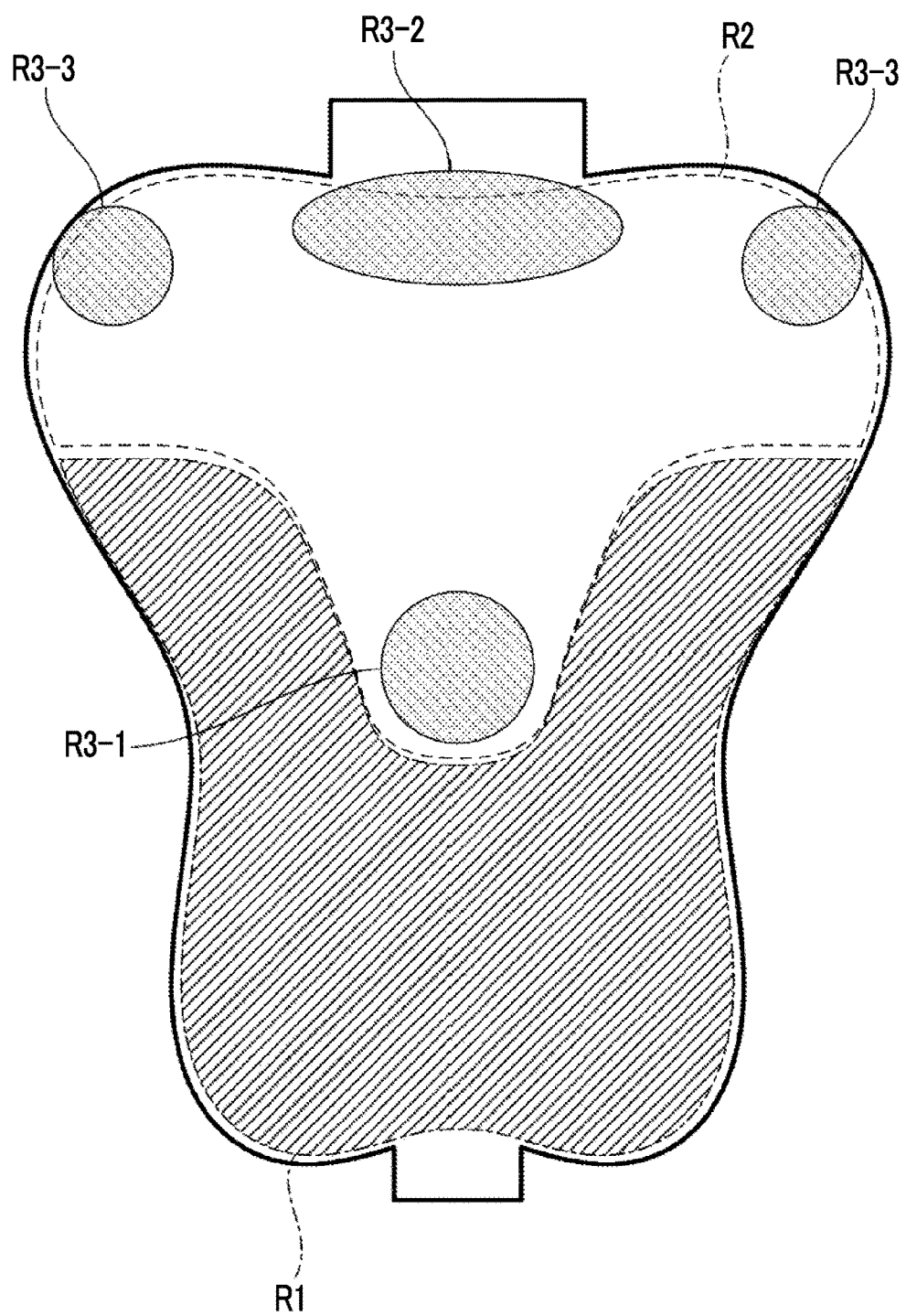
FIG. 12 is a schematic diagram of another display example of the map image shown in FIG. 9.

FIG. 12 shows another display example of a map image.

The example shown in FIG. 12 is a display example of a map image in a case where an essential imaging part is set for the examination target organ. It is assumed that the examination target organ is a stomach and four parts of the pylorus, the gastric angle, the cardia, and the fundus of the stomach are set as essential imaging parts.

The map image shown in FIG. 9 is displayed on the monitor 50 by the control unit 54 (display control unit 64) of the computer 22. The imaged region R1 to which the endoscopic images IMG1 to IMG3 are assigned in the virtual model is displayed with diagonal lines on the map image, and the non-imaged region R2 to which no endoscopic image is assigned in the virtual model is displayed as a blank on the map image.

Among regions on the map images of the four essential imaging parts described above (hereinafter, referred to as essential imaging regions), an essential imaging region R3-1 corresponding to the gastric angle, an essential imaging region R3-2 corresponding to the cardia, and an essential imaging region R3-3 corresponding to the fundus of the stomach overlap the non-imaged region R2.

The control unit 54 (display control unit 64) of the computer 22 generates a notification display for notification of an overlapping region, which overlaps the non-imaged region R2, among the essential imaging regions, and displays the generated notification display on the monitor 50. In the example shown in FIG. 12, the notification display is overlaid on the map image, and is realized by highlighting only the essential imaging regions R3-1 to R3-3 that are overlapping regions. The notification display overlaid on the map image is not particularly limited as long as the notification display is different from the display mode of the non-imaged region R2 excluding the overlapping region. In addition, the notification display is not limited to being overlaid on the map image, and may be a text displayed around the map image.

In this manner, by displaying the notification display for notification of an overlapping region between an essential imaging region corresponding to an essential imaging part and a non-imaged region on the monitor 50 in a case where an essential imaging part is set for the examination target organ, the operator can check whether or not there is omission in imaging of the essential imaging part while advancing the examination. As a result, it is possible to further improve the efficiency of the endoscopic examination.

Up to now, the computer 22 as an image display device installed in the endoscopic examination room Room1 has been described. Hereinafter, the computer 23 as an image display device installed in the conference room Room2 will be described.

Figure 13:
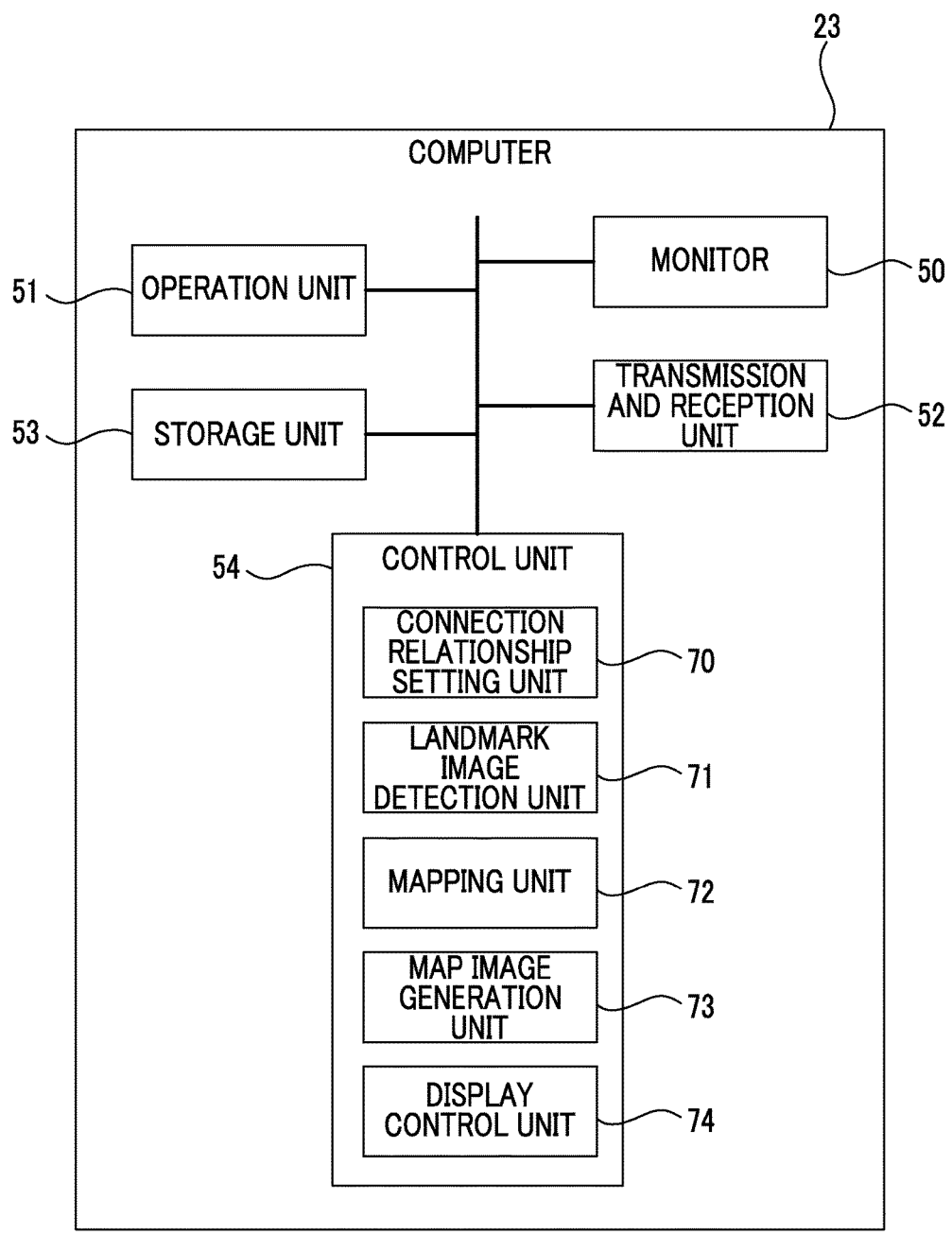
FIG. 13 is a block diagram of another example of the computer as an image display device included in the endoscope department system shown in FIG. 2.

As shown in FIG. 13, the basic configuration of the computer 23 is the same as that of the computer 22. However, the computer 23 collectively acquires all pieces of imaging information including a plurality of interval images captured by the endoscope apparatus 21 through the examination and the imaging order and the imaging condition associated with each of the interval images or all pieces of imaging information including a motion picture captured by the endoscope apparatus 21 through the examination and the imaging order and the imaging condition associated with each frame image forming the motion picture, from the server computer 20 or the PACS 4, after the end of the examination.

In a case where the imaging information includes a plurality of interval images and the imaging order and the imaging condition associated with each of the interval images, each of the plurality of interval images received by the transmission and reception unit 52 is stored in the storage unit 53, as an endoscopic image for map image generation, in a state in which each interval image is associated with the imaging order and the imaging condition.

On the other hand, in a case where the imaging information includes a motion picture and the imaging order and the imaging condition associated with each frame image forming the motion picture, a plurality of frame images are intermittently extracted from the motion picture, and each of the extracted frame images is stored in the storage unit 53, as an endoscopic image for map image generation, in a state in which each frame image is associated with the imaging order and the imaging condition.

The control unit 54 functions as a connection relationship setting unit 70, a landmark image detection unit 71, a mapping unit 72, a map image generation unit 73, and a display control unit 74.

Figure 14:
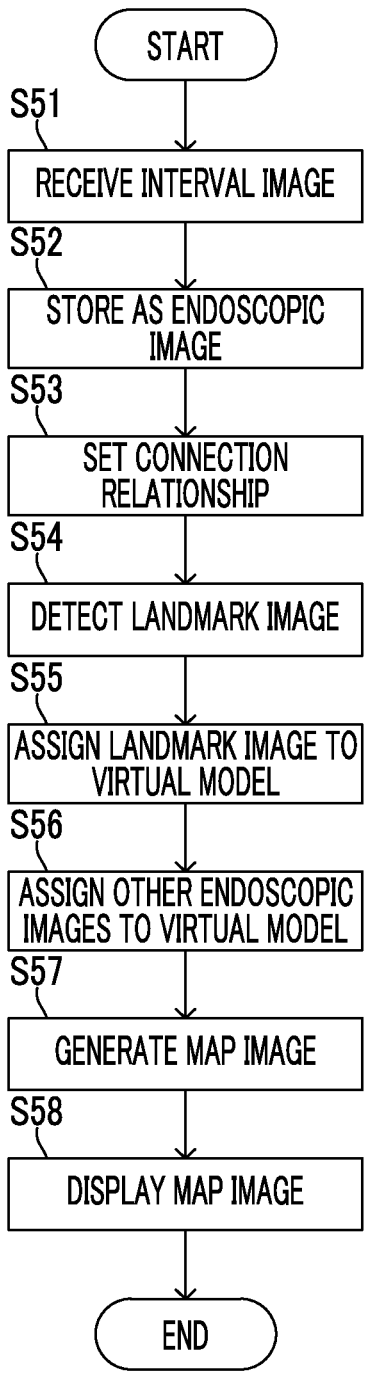
FIG. 14 is a flowchart of an example of processing executed by the computer shown in FIG. 13.
Figure 15:
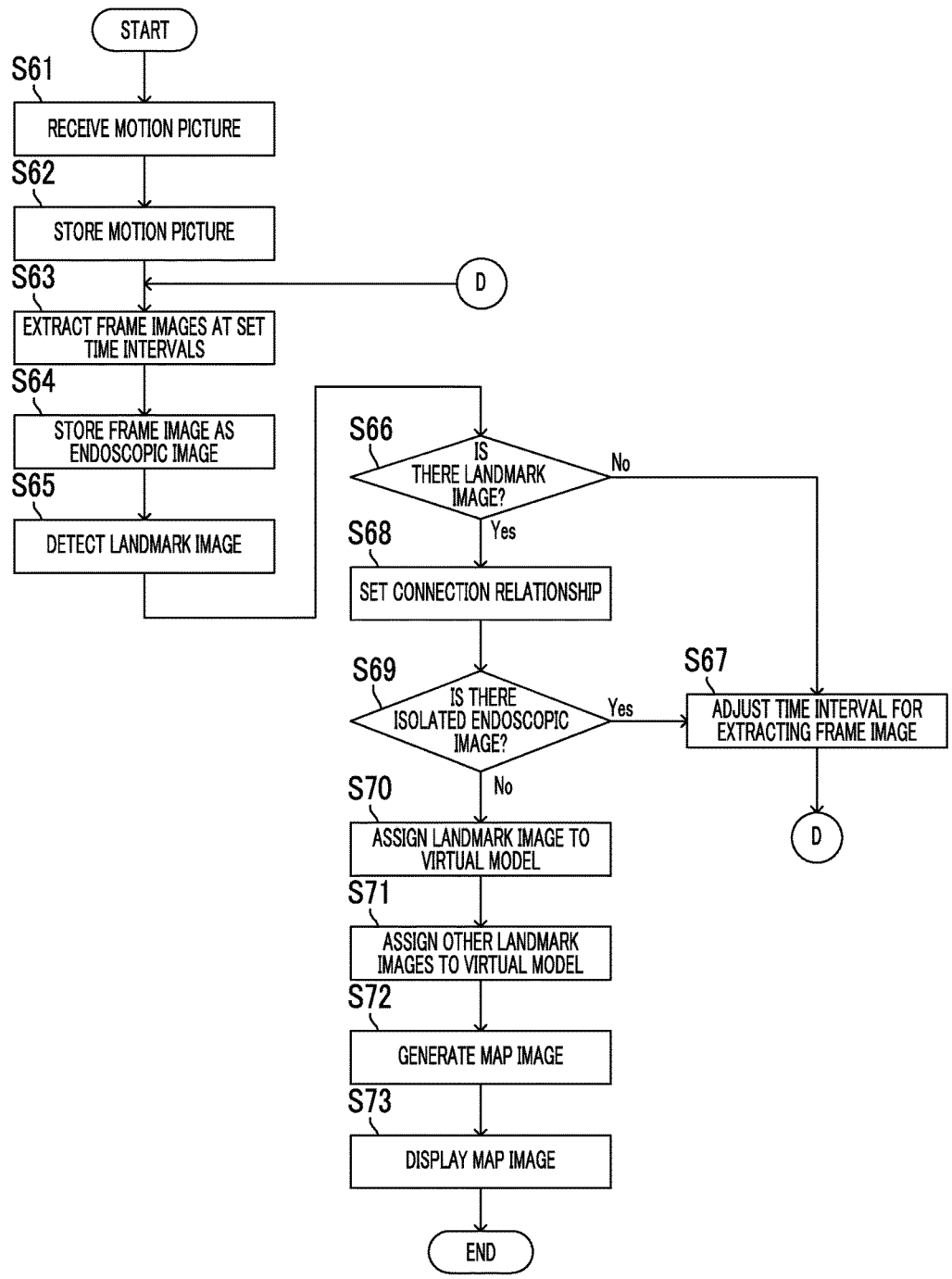
FIG. 15 is a flowchart of another example of the processing executed by the computer shown in FIG. 13.

FIGS. 14 and 15 show an example of the processing of the computer 23.

FIG. 14 shows the processing of the computer 23 in a case where imaging information includes a plurality of interval images and the imaging order and the imaging condition associated with each of the interval images.

First, the control unit 54 of the computer 23 receives imaging information including a plurality of interval images from the server computer 20 or the PACS 4 (step S51), and stores each of the plurality of received interval images in the storage unit 53 as an endoscopic image for map image generation (step S52).

Then, the control unit 54 (connection relationship setting unit 70) sets the connection relationship between the plurality of endoscopic images stored in the storage unit 53 in step S52 (step S53). The connection relationship between endoscopic images can be set using the imaging order associated with the endoscopic images, feature patterns appearing in the images, and the imaging condition (position, posture, and subject distance) associated with the endoscopic images.

Then, the control unit 54 (landmark image detection unit 71) detects a landmark image including an anatomical landmark among the plurality of endoscopic images stored in the storage unit 53 in step S52 (step S54). For example, the anatomical landmark can be detected using a known image matching method, such as feature-based matching and region-based matching.

In a case where an anatomical landmark is included in each of the plurality of endoscopic images, for example, an endoscopic image having the largest proportion of a region occupied by the anatomical landmark may be detected as a landmark image.

Then, the control unit 54 (mapping unit 72) assigns the landmark image to the landmark portion of the virtual model (step S55), and then assigns all other endoscopic images excluding the landmark image to corresponding portions of the virtual model using the connection relationship set in step S53 with the landmark image assigned to the landmark portion as a base point (step S56).

Then, based on the virtual model in which all endoscopic images are assigned to respective portions, the control unit 54 (map image generation unit 73) generates a map image showing an imaged region and a non-imaged region of the imaging target organ (step S57). Then, the control unit 54 (display control unit 74) displays the map image generated in step S57 on the monitor 50 (step S58). As a map image and a map image display method, those shown in FIGS. 9 and 12 can be applied.

FIG. 15 shows the processing of the computer 23 in a case where imaging information includes a motion picture and the imaging order and the imaging condition associated with each frame image forming the motion picture.

First, the control unit 54 of the computer 23 receives imaging information including a motion picture (step S61), and stores the received motion picture in the storage unit 53 (step S62).

Then, the control unit 54 extracts a plurality of frame images from the motion picture stored in the storage unit 53 at set time intervals (step S63), and stores the plurality of frame images extracted in step S63 in the storage unit 53 as endoscopic images for map image generation (step S64).

Then, the control unit 54 (landmark image detection unit 71) detects a landmark image including an anatomical landmark among the plurality of endoscopic images stored in the storage unit 53 in step S64 (step S65).

In a case where no landmark image is detected in the plurality of endoscopic images stored in the storage unit 53 (No in step S66), the control unit 54 performs adjustment, such as shortening the time interval in the case of extracting a plurality of frame images from the motion picture, (step S67). After discarding the plurality of endoscopic images stored in the storage unit 53, the control unit 54 extracts a plurality of frame images again from the motion picture at the adjusted time intervals (step S63), and stores the plurality of extracted frame images in the storage unit 53 as endoscopic images for map image generation (step S64).

In a case where a landmark image is detected in the plurality of endoscopic images stored in the storage unit 53 (Yes in step S66), the control unit 54 (connection relationship setting unit 70) sets the connection relationship between the plurality of endoscopic images stored in the storage unit 53 (step S68).

In a case where there is an endoscopic image that is isolated without being connected to other endoscopic images (Yes in step S69), the control unit 54 performs adjustment, such as shortening the time interval in the case of extracting a plurality of frame images from the motion picture, (step S67). After discarding the plurality of endoscopic images stored in the storage unit 53, the control unit 54 extracts a plurality of frame images again from the motion picture at the adjusted time intervals (step S63), and stores the plurality of extracted frame images in the storage unit 53 as endoscopic images for map image generation (step S64).

In a case where there is no endoscopic image that is isolated without being connected to other endoscopic images (No in step S69), the control unit 54 (mapping unit 72) assigns the landmark image to the landmark portion of the virtual model (step S70), and then assigns all other endoscopic images excluding the landmark image to corresponding portions of the virtual model using the connection relationship set in step S68 with the landmark image assigned to the landmark portion as a base point (step S71).

Then, based on the virtual model in which all endoscopic images are assigned to respective portions, the control unit 54 (map image generation unit 73) generates a map image showing an imaged region and a non-imaged region of the imaging target organ (step S72). Then, the control unit 54 (display control unit 74) displays the map image generated in step S71 on the monitor 50 (step S73). As a map image and a map image display method, those shown in FIGS. 9 and 12 can be applied.

According to the computer 23 as an image display device described above and an image display method executed by the computer 23, it is possible to accurately evaluate omission in imaging in the same manner as in the case of the computer 22 described above. This is useful for ex post evaluation after the end of the examination.

As described above, an image display device disclosed in this specification comprises: a storage unit that stores imaging information including an endoscopic image of an imaging target organ; a connection relationship setting unit that sets a connection relationship between a plurality of endoscopic images stored in the storage unit based on the imaging information; a landmark image detection unit that detects a landmark image including a predetermined anatomical landmark corresponding to the imaging target organ among the plurality of endoscopic images stored in the storage unit; a mapping unit that assigns the landmark image detected by the landmark image detection unit to a landmark portion of a virtual model corresponding to the imaging target organ and that assigns the plurality of endoscopic images stored in the storage unit to corresponding portions of the virtual model using the connection relationship set by the connection relationship setting unit with the landmark image as a base point; a map image generation unit that generates a map image, which shows an imaged region and a non-imaged region of the imaging target organ, based on the virtual model in which the plurality of endoscopic images are assigned to respective portions by the mapping unit; and a display control unit that displays the map image generated by the map image generation unit on a monitor.

In the image display device disclosed in this specification, the imaging information includes an imaging order of the plurality of endoscopic images, and the connection relationship setting unit sets the connection relationship between the plurality of endoscopic images based on the imaging order.

In the image display device disclosed in this specification, the connection relationship setting unit extracts a feature pattern of each of the plurality of endoscopic images, and sets the connection relationship between the plurality of endoscopic images based on the extracted feature pattern.

In the image display device disclosed in this specification, the connection relationship setting unit sets the connection relationship between the plurality of endoscopic images by deforming the endoscopic images which include common feature patterns, so as to match the feature patterns between the endoscopic images.

In the image display device disclosed in this specification, the imaging information includes at least one imaging condition of a position, a posture, or a subject distance of an endoscope in the case of capturing each of the plurality of endoscopic images, and the connection relationship setting unit sets the connection relationship between the plurality of endoscopic images based on the imaging condition.

In the image display device disclosed in this specification, in a case where at least a part of the non-imaged region of the map image generated by the map image generation unit overlaps a predetermined essential imaging region corresponding to the imaging target organ, the display control unit displays a notification display for notification of an overlapping region on the monitor.

In the image display device disclosed in this specification, the display control unit makes a display mode of the overlapping region and a display mode of the non-imaged region excluding the overlapping region different from each other.

In the image display device disclosed in this specification, the plurality of endoscopic images are still images intermittently captured or still images intermittently extracted from a motion picture, the storage unit sequentially stores the still images, the map image generation unit generates the map image each time a predetermined number of new still images are stored in the storage unit, and the display control unit changes a display of the monitor by the map image each time the map image is generated by the map image generation unit.

In the image display device disclosed in this specification, the predetermined number is one.

An image display method disclosed in this specification comprises: a storage step of storing imaging information including an endoscopic image of an imaging target organ in a storage unit; a connection relationship setting step of setting a connection relationship between a plurality of endoscopic images stored in the storage unit based on the imaging information; a landmark image detection step of detecting a landmark image including a predetermined anatomical landmark corresponding to the imaging target organ among the plurality of endoscopic images stored in the storage unit; a mapping step of assigning the detected landmark image to a landmark portion of a virtual model corresponding to the imaging target organ and assigning the plurality of endoscopic images stored in the storage unit to corresponding portions of the virtual model using the connection relationship set in the connection relationship setting step with the landmark image as a base point; a map image generation step of generating a map image, which shows an imaged region and a non-imaged region of the imaging target organ, based on the virtual model in which the plurality of endoscopic images are assigned to respective portions; and a display step of displaying the generated map image on a monitor, wherein the storage step, the connection relationship setting step, the landmark image detection step, the mapping step, the map image generation step, and the display step are executed by a computer.

In the image display method disclosed in this specification, the plurality of endoscopic images are still images intermittently captured or still images intermittently extracted from a motion picture, in the storage step, the still images are sequentially stored in the storage unit, in the map image generation step, the map image is generated each time a predetermined number of new still images are stored in the storage unit, and in the display step, a display of the monitor is changed by the map image each time the map image is generated in the map image generation step.

A program disclosed in this specification causes a computer to execute each of the steps described above. The program can be provided by being recorded on a computer-readable non-transitory recording medium. The "computer-readable recording medium" includes an optical medium, such as a compact disc-ROM (CD-ROM), and a magnetic recording medium, such as a memory card. The program can also be provided by downloading through a network.

What is claimed is:

1. An image display device, comprising:
 a storage that stores imaging information including an endoscopic image of an imaging target organ; and
 a processor configured to:
  set a connection relationship between a plurality of endoscopic images stored in the storage based on the imaging information;
  detect a landmark image including a predetermined anatomical landmark corresponding to the imaging target organ among the plurality of endoscopic images stored in the storage;
  assign the landmark image that is detected to a landmark portion of a virtual model corresponding to the imaging target organ and assign the plurality of endoscopic images stored in the storage to corresponding portions of the virtual model using the connection relationship that is set with the landmark image as a base point;
  generate a map image, which shows an imaged region and a non-imaged region of the imaging target organ, based on the virtual model in which the plurality of endoscopic images are assigned to respective portions; and
  display the map image that is generated on a monitor.

2. The image display device according to claim 1, wherein the imaging information comprises an imaging order of the plurality of endoscopic images, and the processor is further configured to set the connection relationship between the plurality of endoscopic images based on the imaging order.

3. The image display device according to claim 1, wherein the processor is further configured to extract a feature pattern of each of the plurality of endoscopic images, and set the connection relationship between the plurality of endoscopic images based on the extracted feature pattern.

4. The image display device according to claim 2, wherein the processor is further configured to extract a feature pattern of each of the plurality of endoscopic images, and set the connection relationship between the plurality of endoscopic images based on the extracted feature pattern.

5. The image display device according to claim 3, wherein the processor is further configured to set the connection relationship between the plurality of endoscopic images by deforming the endoscopic images which include common feature patterns, so as to match the feature patterns between the endoscopic images.

6. The image display device according to claim 4, wherein the processor is further configured to set the connection relationship between the plurality of endoscopic images by deforming the endoscopic images which include common feature patterns, so as to match the feature patterns between the endoscopic images.

7. The image display device according to claim 1, wherein the imaging information comprises at least one imaging condition selected from a position, a posture and a subject distance of an endoscope at a time of capturing each of the plurality of endoscopic images, and the processor is further configured to set the connection relationship between the plurality of endoscopic images based on the imaging condition.

8. The image display device according to claim 2, wherein the imaging information comprises at least one imaging condition selected from a position, a posture and a subject distance of an endoscope at a time of capturing each of the plurality of endoscopic images, and the processor is further configured to set the connection relationship between the plurality of endoscopic images based on the imaging condition.

9. The image display device according to claim 1, wherein, in a case where at least a part of the non-imaged region of the map image generated by the processor overlaps a predetermined essential imaging region corresponding to the imaging target organ, the processor is further configured to display a notification display for notification of an overlapping region on the monitor.

10. The image display device according to claim 2, wherein, in a case where at least a part of the non-imaged region of the map image generated by the processor overlaps a predetermined essential imaging region corresponding to the imaging target organ, the processor is further configured to display a notification display for notification of an overlapping region on the monitor.

11. The image display device according to claim 9, wherein the processor is further configured to make a display mode of the overlapping region and a display mode of the non-imaged region excluding the overlapping region different from each other.

12. The image display device according to claim 10, wherein the processor is further configured to make a display mode of the overlapping region and a display mode of the non-imaged region excluding the overlapping region different from each other.

13. The image display device according to claim 1, wherein the plurality of endoscopic images are still images intermittently captured or still images intermittently extracted from a motion picture, the storage sequentially stores the still images, the processor is further configured to generate the map image each time a predetermined number of new still images are stored in the storage, and the processor is further configured to change a display of the monitor by the map image each time the map image is generated.

14. The image display device according to claim 2, wherein the plurality of endoscopic images are still images intermittently captured or still images intermittently extracted from a motion picture, the storage sequentially stores the still images, the processor is further configured to generate the map image each time a predetermined number of new still images are stored in the storage, and the processor is further configured to change a display of the monitor by the map image each time the map image is generated by the map image generation unit.

15. The image display device according to claim 13, wherein the predetermined number is one.

16. The image display device according to claim 14, wherein the predetermined number is one.

17. An image display method, comprising:

a storage step of storing imaging information including an endoscopic image of an imaging target organ in a storage unit;

a connection relationship setting step of setting a connection relationship between a plurality of endoscopic images stored in the storage unit based on the imaging information;

a landmark image detection step of detecting a landmark image including a predetermined anatomical landmark corresponding to the imaging target organ among the plurality of endoscopic images stored in the storage unit;

a mapping step of assigning the detected landmark image to a landmark portion of a virtual model corresponding to the imaging target organ and assigning the plurality of endoscopic images stored in the storage unit to corresponding portions of the virtual model using the connection relationship set in the connection relationship setting step with the landmark image as a base point;

a map image generation step of generating a map image, which shows an imaged region and a non-imaged region of the imaging target organ, based on the virtual model in which the plurality of endoscopic images are assigned to respective portions; and a display step of displaying the generated map image on a monitor, wherein the storage step, the connection relationship setting step, the landmark image detection step, the mapping step, the map image generation step and the display step are executed by a computer.

18. The image display method according to claim 17, wherein the plurality of endoscopic images are still images intermittently captured or still images intermittently extracted from a motion picture, in the storage step, the still images are sequentially stored in the storage unit, in the map image generation step, the map image is generated each time a predetermined number of new still images are stored in the storage unit, and in the display step, a display of the monitor is changed by the map image each time the map image is generated in the map image generation step.

19. A non-transitory computer readable medium storing a program causing a computer to execute:

a storage step of storing imaging information including an endoscopic image of an imaging target organ in a storage unit;

a connection relationship setting step of setting a connection relationship between a plurality of endoscopic images stored in the storage unit based on the imaging information;

a landmark image detection step of detecting a landmark image including a predetermined anatomical landmark corresponding to the imaging target organ among the plurality of endoscopic images stored in the storage unit;

a mapping step of assigning the detected landmark image to a landmark portion of a virtual model corresponding to the imaging target organ and assigning the plurality of endoscopic images stored in the storage unit to corresponding portions of the virtual model using the connection relationship set in the connection relationship setting step with the landmark image as a base point;

a map image generation step of generating a map image, which shows an imaged region and a non-imaged region of the imaging target organ, based on the virtual model in which the plurality of endoscopic images are assigned to respective portions; and a display step of displaying the generated map image on a monitor.

\* \* \* \* \*